United States Patent [19]

Sachs et al.

[11] 4,452,249
[45] Jun. 5, 1984

[54] MICROELECTRODES AND PROCESS FOR SHIELDING SAME

[75] Inventors: Frederick Sachs, Buffalo; Richard G. McGarrigle, Eggertsville, both of N.Y.

[73] Assignee: The Research Foundation of State University of New York, Albany, N.Y.

[21] Appl. No.: 326,388

[22] Filed: Dec. 1, 1981

[51] Int. Cl.³ .............................................. A61B 5/04
[52] U.S. Cl. .................................. 128/642; 204/403; 427/125; 427/273
[58] Field of Search .......... 204/195 R, 195 G, 195 L, 204/195 M; 128/642, 635, 784; 427/58, 79, 81, 125, 273; 134/2; 156/656

[56] References Cited

U.S. PATENT DOCUMENTS 3,205,155  9/1965  Natter ................................. 156/656
3,436,329  4/1969  Kahn et al. ...................... 204/195 R
4,207,138  6/1980  Hitch .............................. 156/656 X

FOREIGN PATENT DOCUMENTS 695655  11/1979  U.S.S.R. ............................. 128/642

OTHER PUBLICATIONS

E. J. Thompson, An Improved Method for Extracellular Recording of Action Potentials from Single Cultured Neuroblastoma Cells, M. B. E., v. 13, #1, 1/75, pp. 104–106.
An Almost Completely Shielded Microelectrode, F. Sachs and R. McGarrigle, (Journal of Neuroscience Methods), 3, (1980), pp. 151–157.

Primary Examiner—G. L. Kaplan
Assistant Examiner—Nam X. Nguyen
Attorney, Agent, or Firm—Michael L. Dunn; Howard M. Ellis

[57] ABSTRACT

A shielded microelectrode process and product wherein the microelectrode is coated by vacuum evaporation techniques with a thin layer of silver; the silver from the microelectrode tip region is removed to a depth of no greater than substantially 20 micrometers by contact with memory; and the microelectrode is dipped into a thermosetting wax in liquid form whereby as the wax solidifies the silver is coated thereby below the tip region.

11 Claims, 4 Drawing Figures

MICROELECTRODES AND PROCESS FOR SHIELDING SAME

BACKGROUND OF THE INVENTION

The present invention relates to microelectrodes and to a process for shielding the same.

Microelectrodes are widely used in electrophysiology for recording potentials, passing currents or for iontophoresis. These microelectrodes are usually fabricated of glass pipettes having a central opening therethrough, the tip of which is adapted to be placed in a tissue bath or the like for the above-mentioned sensing or probing purposes. However, at audio frequencies, the electrode capacitance to the tissue bath and to adjacent electrodes can cause interference and reduced fidelity. In an attempt to overcome these problems various techniques of or forms of electrical shielding have been proposed.

For example, the provision of a driven shield over a voltage recording electrode has the desirable effect of reducing the effective capacitance of the electrode to thereby permit higher bandwidth recordings. During iontophoresis and recording employing a multiple barrel pipette or electrode, the response time of the recording pipette is reduced due to the pipettes capacitance to the neighboring iontophoretic barrels as well as its capacitance to the tissue bath. In addition, voltage fluctuations generated by the passage of current through the iontophoretic barrels can cause electrical noise in the recording barrel. Electrodes are known wherein a graphite aerosol has been used to shield the recording microelectrode to within 1 mm of the tip thereof. For a typical microelectrode-to-bath capacity of 1 $pF/mm$, however, this 1 mm tip exposure produces too much capacitance for more demanding application such as microelectrode voltage clamping or high fidelity impedance measuring.

One of the major drawbacks in the employment of microelectrode voltage clamps is the unavoidable capacitance between the current and the voltage electrodes which combines with the resistance thereof to form an R C circuit to thereby introduce a time lag or constant that significantly slows down the response or recording process. Electronic compensation has been proposed, in an attempt to overcome this problem, by partially cancelling the interelectrode capacities. However, the success of such electrode compensation techniques is subject to the variabilities in the electrodes themselves, foremost among which is the resistance of the current electrode. Further, such compensation techniques introduce excessive noise in that amplifier noise fed through the compensation capacity is added to the membrane potential. It is, therefore, extremely crucial to reduce or minimize the capacity between the current and voltage electrodes.

Heretofore, the common method of shielding microelectrodes is to simply apply silver paint to the same with the aid of a suitably powered microscope. However, the grain size of silver paint is large and the painting process is tedious, especially if it is desired to shield close to the tip of the microelectrode.

SUMMARY OF THE INVENTION

The foregoing problems, as well as other problems not specifically mentioned, are overcome according to the teachings of the present invention, which provides a microelectrode and process for shielding and insulating the same whereby a conductive layer of shielding material is coated exteriorly thereof to within substantially 20 micrometers or less of the tip thereof and is sandwiched between an insulating layer extending below the conductive layer and adhering to the electrode without clogging the central throughopening at the tip thereof.

In the context of the present invention in order to optimally shield the microelectrodes the shield:

1. must be highly conductive;
2. must not interfere with penetration;
3. must be insulated from the surrounding aqueous media; and
4. should lend itself to relatively simple and repeatable construction.

That these requirements are adequately satisfied according to the teachings of the present invention will become apparent hereinbelow.

Essentially the method according to the invention includes the steps of; coating the exterior surface of a microelectrode having a central throughopening by vacuum evaporation techniques to provide a thin layer of conductive material thereabout; removing a controlled layer of conductive material from a circumferential tip area of the microelectrode leaving a tip region thereof exposed; and inserting said microelectrode into an insulating material in liquid form whereby as the insulating material solidifies about the microelectrode the layer of conductive material and a portion of the tip region is completely covered thereby leaving the remainder of the tip region and the central throughopening of the microelectrode fully exposed.

The evaporative deposition provides a very thin uniform layer of highly conductive material without clogging the open tip of the microelectrode, whereas the liquid insulating material adequately provides a complete dielectric covering for the conductive material without, similarly, clogging the tip opening and, yet, leaving a very small thin-walled electrode tip for adequate penetration into the tissue bath, incidental to the routine use thereof.

The resulting shielded microelectrode product according to the present invention including a microelectrode body; a central throughopening passing from the shank end of the body to the operative tip end thereof; a coating of conductive material adhering in surrounding relation to the exterior of the body short of the tip thereof to thereby leave an exposed exterior tip portion of no greater than 20 micrometers.

In this manner the capacitance of the exposed tip region is reduced to a minimum and, consequentially, the above-noted capacitance-related problems are significantly reduced, if not entirely eliminated.

BRIEF DESCRIPTION OF THE DRAWINGS

For a fuller understanding of the present invention and its characterizing features reference should now be made to the following detailed description thereof taken in conjunction with the accompanying drawings, wherein.

DETAILED DESCRIPTION OF THE PREFERRED EMBODIMENT

Figure 1:
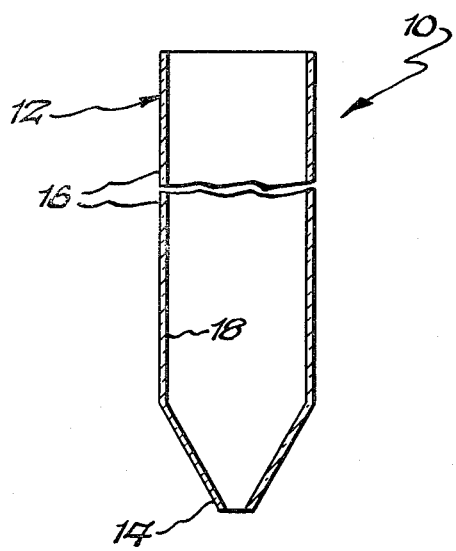
FIG. 1 is a schematic cross-sectional view of the microelectrode, greatly enlarged for ease in illustration.

In practising the method of the present invention a standard microelectrode is employed, as depicted generally at 10 in FIG. 1. Electrode 10 is of needle-like construction having a shank end 12, a tapered operative tip end 14, an exterior surface 16 and a hollow interior through passage or opening 18, extending from the shank end to the tip end. Microelectrode 10 may be suitably fabricated of glass.

Figure 2:
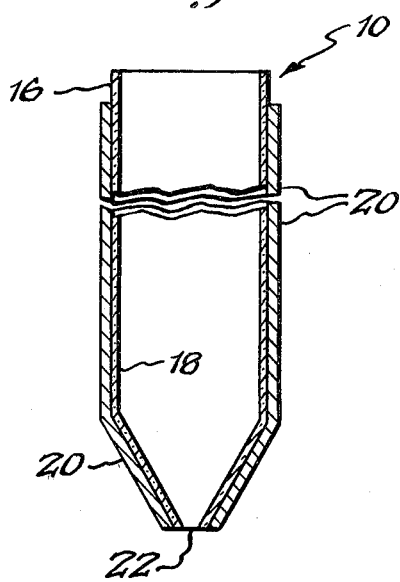
FIG. 2 is a view similar to FIG. 1 but depicting the microelectrode after the same has been coated with the thin layer of conductive or shielding material.

A suitable highly conductive material, such as silver or gold from the noble metal group is completely deposited on the microelectrode 10 to form a thin uniform layer of conductive metal 20, as depicted in FIG. 2, without clogging the tip opening 22 of the microelectrode. To accomplish this coating process any well known vacuum evaporation techniques may be employed. For example, the microelectrode may be placed tip up on a Teflon disk drilled to accommodate about 50 electrodes. The disk and electrodes, after being rinsed in acetone may then be attached to the shaft of a sample rotator in a vacuum evaporator of the type used for shadowing in electron microcopy. Next, a few hundred milligrams of silver wire may be placed in an evaporation basket at a distance of approximately 10 cm from the electrodes and the evaporation is run to completion (about 4 minutes). The evaporation leaves the electrodes completely coated with silver except for about 3 to 4 cm at the shank end 16.

Figure 3:
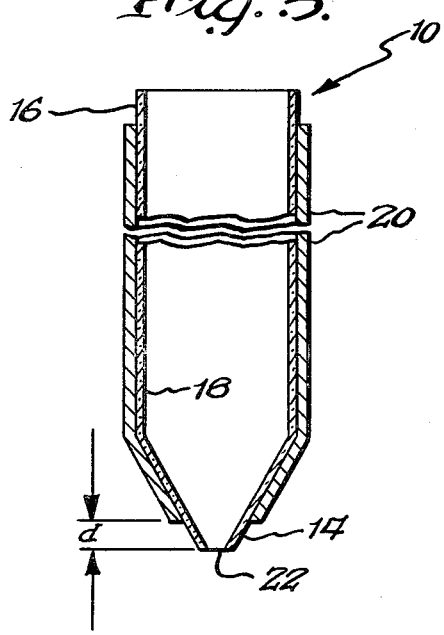
FIG. 3 is a view similar to FIG. 2 but depicting the microelectrode after removal of the conductive layer from a tip region thereof.

The next step in the process is to remove a controlled amount of the conductive material (silver in this example) from the tip of the microelectrode. To this end, the electrode may be mounted in a micromanipulator observed under a microscope and the tip thereof may be touched to a small ball of mercury resting in a petri dish. The silver and mercury form an amalgam which immediately dissolves the silver from the tip 14. The negative meniscus of the mercury prevents the same from creeping up the electrode such that by careful manipulation, the silver may be removed in a controlled fashion for distances of only a few micrometers from the electrode tip. In fact, as shown at d in FIG. 3, it is possible to reduce the tip exposure to a depth of 20 micrometers or less. This step is simple, reliable, and, most importantly, does not clog the tip of the electrode.

It is to be understood that other methods and/or mechanisms for conductive material removal are contemplated within the scope of the present invention.

Figure 4:
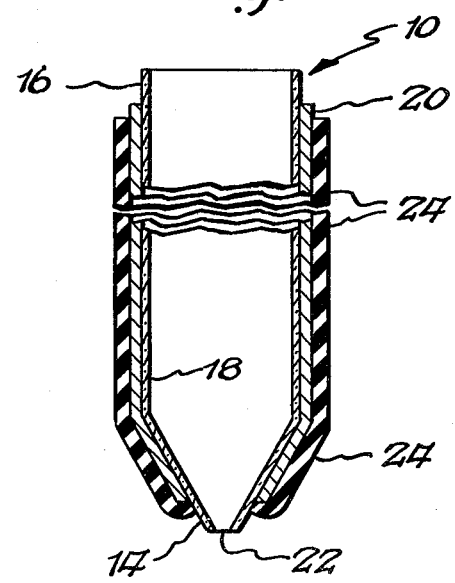
FIG. 4 is a view similar to FIG. 3 but depicting the final microelectrode product after the insulation has been applied thereto.

The final step of the present invention is that of insulating the shielded microelectrode. It has been found that dipping the electrode, tip first, in a bath or reservoir of liquid insulating material of proper viscosity and surface tension results in satisfactory insulating coatings which leave the electrode tip clear and unclogged, as depicted at 24 in FIG. 4. More specifically, the electrode is dipped into a vial or the like of liquid insulating material and held tip down for a few seconds and removed to allow the insulating material to harden. Surface tension withdraws excess insulating material upwardly along the tapered tip 14 of the electrode to thereby leave the tip clear and unclogged and to provide a hardened layer of material that completely surrounds and insulates the conductive layer or shield 20. Examples of insulating material evidencing satisfactory results and having desirable properties of viscosity and surface tension in their liquid state are "Crown Sticky Wax" manufactured by S. S. White of Philadelphia, Pa. and "Pyseal" C-228 available from Fisher Scientific. It has been found that the "Crown Sticky Wax" should be conditioned after being melted by boiling the same for a few hours until the liquid turns from its original rust color to a dull green. With the "Pyseal" wax, no such conditioning has been required. It should be understood, however that any other suitable insulating material or thermosetting waxes exhibiting similar viscosity and surface tension properties are contemplated within the scope of the present invention.

It should, thus, be apparent that the process and product of the present invention accomplishes its objectives of simply, yet accurately, shielding the microelectrode tip to a depth of 20 micrometers or less, and insulating the same to a resistance of at least $10^{10}$ ohms with stray capacitance thereat reduced to about 1 pF/mm of exposed tip. Thus, for 20 micrometers of exposed tip, stray capacitance would be only about 20 fF.

Although a preferred embodiment of the method and product of the present invention has been disclosed and described, changes will obviously occur to those skilled in the art without departing from the spirit thereof. It is therefore intended that the same is to be limited only by the scope of the appended claims.

What is claimed is:

1. A method of shielding microelectrodes, including the steps of:
   coating the exterior surface of a microelectrode having a central throughopening by vacuum evaporation techniques to provide a thin layer of conductive material thereabout; and
   removing a controlled layer of conductive material from a circumferential tip area of said microelectrode leaving a tip region thereof exposed.

2. The method according to claim 1, wherein:
   said step of removing comprises contacting said tip area with mercury whereby said conductive material is dissolved without clogging said central throughopening.

3. The method according to claim 2, wherein:
   said conductive material is silver.

4. The method according to claim 2, wherein:
   said conductive material is chosen from the noble metal group.

5. The method according to claim 4, wherein:
   said controlled layer of conductive material is removed to a depth no greater than substantially 20 micrometers from said tip.

6. The method according to any one of claims 1, 2, 4, or 5 further comprising the step of:
   dipping said microelectrode, tip first, into a liquid insulating material whereby as the insulating material solidifies about the microelectrode said layer of conductive material and a portion of said tip region is completely covered by said insulating material leaving the remainder of said tip region and said central throughopening fully exposed.

7. The method according to claim 6, wherein:
   said insulating material comprises a thermosetting wax.

8. A shielded microelectrode, comprising:
   a microelectrode body having a throughopening extending from a shank end of said body to the operative tip end thereof;

a thin layer of conductive material applied to said microelectrode body by vacuum evaporation, said conductive material adhering in surrounding relation to the exterior of said body short of the tip thereof to thereby leave an exposed exterior tip portion of no greater than substantially 20 micrometers, and a layer of insulating material covering said conductive material and a portion of said exposed tip.

9. The microelectrode according to claim 8 wherein: said conductive material is chosen from the noble metal group.

10. The microelectrode according to claim 9 wherein: said insulating material comprises a thermosetting wax.

11. The microelectrode according to claim 9, wherein: said conductive material is silver.

* * * * *

UNITED STATES PATENT AND TRADEMARK OFFICE
CERTIFICATE OF CORRECTION

PATENT NO. : 4,452,249
DATED : June 5, 1984
INVENTOR(S) : Frederick Sachs and Richard G. McGarrigle It is certified that error appears in the above-identified patent and that said Letters Patent are hereby corrected as shown below:

Cover page, ABSTRACT, line 6 "memory" should read "mercury".

Signed and Sealed this

Third Day of February, 1987

Attest:

DONALD J. QUIGG

Attesting Officer

Commissioner of Patents and Trademarks